United States Patent [19]

Alcidi

[11] 4,009,721
[45] Mar. 1, 1977

[54] ARTIFICIAL PACEMAKER
[75] Inventor: Mario Alcidi, Florence, Italy
[73] Assignee: Pacer S.n.C. of Cerchiai Vanna & C., Italy
[22] Filed: Apr. 23, 1976
[21] Appl. No.: 679,742
[30] Foreign Application Priority Data
  Apr. 24, 1975 Italy ................................. 9412/75
[52] U.S. Cl. ........................ 128/419 PG; 128/2 P
[51] Int. Cl.² ........................................... A61N 1/36
[58] Field of Search ............... 128/1 D, 2 E, 2.1 E, 128/419 P, 419 PG, 419 PS, 419 R, 421, 422, 423, 260

[56]   References Cited
       UNITED STATES PATENTS

| 3,349,989 | 10/1967 | Reynolds | 128/419 PS |
| 3,421,512 | 1/1969 | Frasier | 128/419 PG |
| 3,593,718 | 7/1971 | Krasner et al. | 128/419 PG |
| 3,739,279 | 6/1973 | Hollis | 128/2 P |
| 3,923,060 | 12/1975 | Ellinwood, Jr. | 128/260 |

*Primary Examiner*—William E. Kamm
*Attorney, Agent, or Firm*—McGlew and Tuttle

[57] ABSTRACT

The pacemaker comprises an indicating micro-electrode in association with a reference electrode and inserted in the patient's body in contact with the blood to measure the pH of the blood. This measuring device is connected, through an impedance adapter, to the input of an amplifier which amplifies the mV output of the measuring device by at least a thousand times, and the output of the amplifier is supplied to the input of a transistorized oscillator generating signals of variable frequency in accordance with its input. The oscillator is connected to a cathode follower to furnish the energy necessary for the impulses for the cardiac stimulation which, as known, are applied to an electrode inserted in the cardiac muscular tissue of the ventricle of the heart. A limiter is connected to the input of the amplifier. The amplifier may be either a direct current amplifier or an alternating current amplifier.

16 Claims, 2 Drawing Figures

ARTIFICIAL PACEMAKER

FIELD AND BACKGROUND OF THE INVENTION

It is known that atrial ventricular blockages are today cured easily by means of an electrical cardiac stimulator or artificial pacemaker which, through an electrode inserted in the cardiac muscular tissue of the ventricle, transmits, to the heart, continuously and with the same rhythm, electrical stimuli capable of making the heart beat regularly. It has been proven that persons wearing an artificial pacemaker, especially if it is implanted subcutaneously and provided with long-lasting batteries, have a work capacity not significantly lower than normal, even with respect to activities which require muscular effort.

The limits to the muscular effort which can be exerted by wearers of artificial pacemakers are today imposed by the impossibility, on the part of the pacemaker, to self-regulate the frequency of the stimuli delivered and, consequently, of the heart beat, more especially to increase the cardiac output in response to the increased metabolic requirements of the body.

It is a known fact that, when a person exerts an effort, the body presents a hemodynamic picture characterized by the following:

a. the heart increases its beat frequency up to double the usual frequency and triple the frequency, in linear and direct ratio to given values, as the intensity and duration of the physical effort increases;

b. within a certain frequency of the contractions, the heart increases the systolic output as the physical effort increases, the increase in frequency of contractions and the increase in systolic output combining to increase the cardiac output so as to furnish the oxygen requirements; and c. the peripheral resistances, and thus also the systolic pressure, increase.

The body, when exerting a physical effort, also presents a metabolic picture with the increase in muscular efforts, as follows:

a. the lactic acid increases;
b. the $pCO_2$ increases;
c. the $PO_2$ decreases in the arterial blood; and
d. the hydrogen ion concentration increases in the coronary, veinous and arterial blood, which is equivalent to a reduction of the pH.

Considering now a subject with stable atrio-ventricular block, or with atrial-ventricular block controlled by an artificial pacemaker of fixed frequency, the metabolic picture presents more marked variations, since the hemodynamic picture is deficient due to the fact that the cardiac output increases only a little and with difficulty, through the increase in systolic pressure alone, with the result of early fatigue and the impossibility of continuing the physical effort.

SUMMARY OF THE INVENTION

The object of the present invention is an improved artificial pacemaker whose chief characteristic is to regulate the frequency of the signals delivered to the heart in accordance with the metabolic needs of the wearer's body, and this is of particular importance when the wearer is performing muscular work or exerting a muscular effort. The invention is based on the principle that, during the performance of muscular work and especially if the work is intense and prolonged in time, in the metabolic picture pH, the $pO_2$ and the $pCO_2$ of the human blood undergo a modification, namely a reduction of the pH and $pO_2$ and an increase of the $pCO_2$, and that, simultaneously, in the hemodynamic picture, the beat frequency undergoes an increase to obtain a greater cardiac output, which represents the natural and necessary response to the increase in oxygen consumption by the tissues.

The present invention has numerous advantages. Thus, a first advantage is the obtaining of self regulation of the frequency of the stimulation signals emitted by the pacemaker as a function of the work performed by the wearer and determined by the instantaneous variation of the pH of the blood.

A further advantage is the continuous electrometric measurement of the blood, and another advantage is the high sensitivity for the purpose of appraising small pH variations of the blood, namely of the order of 0.01.

Still another advantage is the prompt response of the invention pacemaker to the detected variation of the pH of the blood.

Another advantage is the ability to fix the maximum and minimum limit values of the frequency of stimulation, together with the ability to fix the pH scanning interval, all in relation to the working capacities of the patient. This also permits the exclusion of the self-regulation, so that the pacemaker can operate in the conventional manner, if necessary.

An object of the invention is to provide an improved artificial pacemaker.

Another object of the invention is to provide such a pacemaker capable of regulating the frequency of the signals delivered in relation to the metabolic needs of the wearer's body.

A further object of the invention is to provide such a pacemaker in which the regulation of the frequency of the stimulation signals emitted by the pacemaker is a function of the work performed by the wearer and determined by the instantaneous variation of pH of the blood.

For an understanding of the principles of the invention, reference is made to the following description of typical embodiments thereof as illustrated in the accompanying drawing.

DESCRIPTION OF THE PREFERRED EMBODIMENTS

Figure 1:
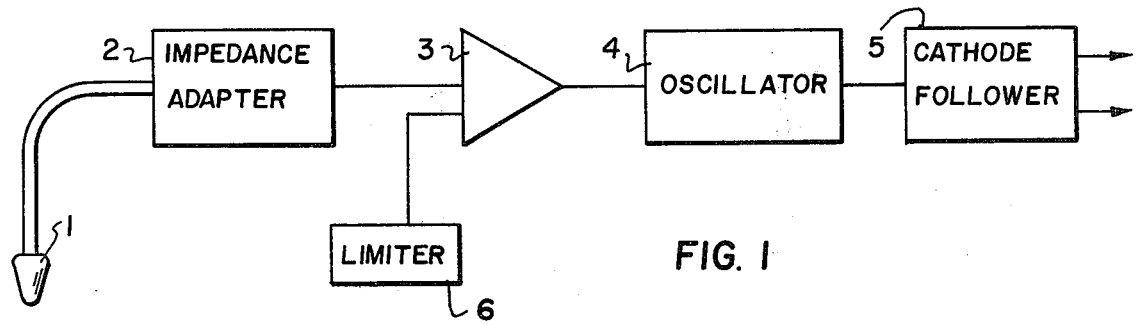
FIG. 1 is a block diagram of an improved electric pacemaker embodying the invention and using a d.c. amplifier.

Reduced to its essential structure, an improved artificial pacemaker embodying the present invention comprises, as shown in FIG. 1, a device 1 for the continuous electrometric measurement of the pH of the blood, an active impedance adapter 2, a d.c. amplifier 3, an oscillator 4, a cathode follower 5, and a limiting circuit or limiter 6, as shown in block form in FIG. 1.

More particularly, for the electrometric measurement of the pH in the blood, any pH indicating-reading electrode may be used, preferably an electrode of the metal-metal oxide type with a metal preferably of the platinum family. The reference electrode associated with the indicating-reading electrode is preferably silver-silver chloride in sodium chloride solution, but any suitable reference electrode may be used provided that it is not polarizable.

The materials used for the indicating-reading electrode, namely iridium or other metals of the platinum family, as well as for the insulating coating of this electrode, namely "SILASTIC" which is a silicone rubber composition particularly designed for use in prosthetic applications, are commonly used in the electric catheters of conventional pacemakers. The reference electrode is placed out of contact with the blood, although constituting one of the components of the pacemaker.

The electrical circuit of the indicating-reading electrode and the reference electrode is completed by a high impedance, of the order of several GOhms, of the active impedance adapter 2. The d.c. amplifier 3 connected to the output of adapter 2 is operable to amplify, by at least one thousand times, the signal coming from the indicating micro-electrode, and which has a potential of the order of a few mV.

The oscillator 4, connected to the output of amplifier 3, is preferably a solid state oscillator of the astable type, which is transistorized, and has a function of generating signals of a variable frequency with the frequency variation being obtained by polarization of the bases of the transistors of the oscillator by means of the signal derived from amplifier 3. The cathode follower 5, connected to the oscillator 4, furnishes the energy necessary for the impulses for cardiac stimulation. Limiting circuit 6 is provided to fix the values of the maximum and minimum frequencies of the signal for the stimulation, and also to set the pH scanning interval.

Figure 2:
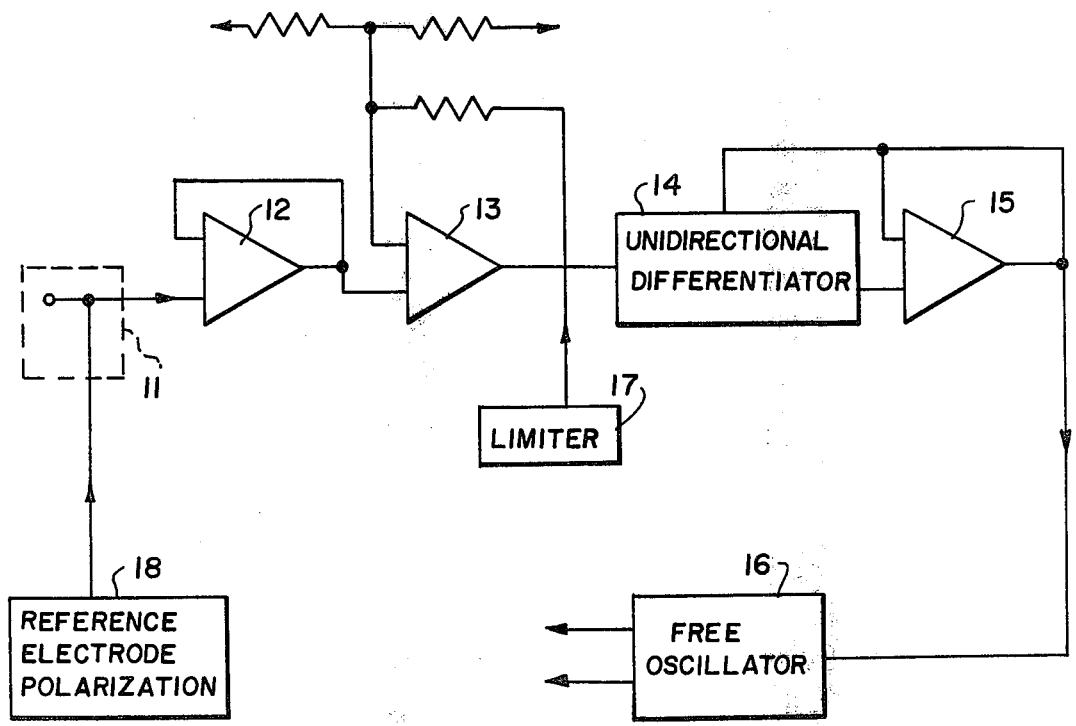
FIG. 2 is a block diagram of the improved electric pacemaker embodying the invention and using an a.c. amplifier.

The embodiment of the pacemaker of the invention shown in FIG. 2 differs from that shown in FIG. 1 essentially only in using an a.c. amplifier. The circuit of FIG. 2 has further advantages including a greater stability in time and an insensitivity to slow varitions of the signals, that is, drift of any origin including the discharge of the batteries. This insensitivity to slow variations of the signals applies also to physiological variations, and is hence significant of the parameter of the pH of the blood. However, this would appear to be of secondary importance in consideration of the fact that variations of the pH of the blood, when the wearer of the pacemaker is exerting muscular effort, are always very rapid.

Referring more particularly to FIG. 2, the improved artificial pacemaker embodying the invention as shown therein comprises a device 11 for the continuous electrometric measurement of the pH of the blood, an active impedance adapter 12, an amplifier 13, a unidirectional differentiator 14, an a.c. amplifier 15, a free oscillator, or conventional pacemaker 16, an operation limiting circuit 17, and a reference electrode polarization circuit 18.

In greater detail, the indicating-reading electrode and the reference electrode are of the type mentioned above with respect to the embodiment of the invention shown in FIG. 1. The electric circuit of the indicating-reading electrode includes, in series, a high impedance, of the order of about $10^{12}$ Ohms, of the active impedance adapter 12. The amplifier 13 connected to the output of adapter 12 is capable of amplifying, by about 100 times, the signal coming from the indicating-reading microelectrode, so as to obtain useful output signals of the order of 1 volt.

The unidirectional differentiator 14 connected to the output of amplifier 13 has the function of discriminating the useful signals from those due to drifts of any origin, and has the further function of rendering the system insensitive to the alkaline variations, that is, of preventing the stimulus frequency from falling below a predetermined minimum value.

The a.c. amplifier 15, connected to the output of unidirectional differentiator 14, has the function of furnishing, at its output circuit, a signal capable of piloting the oscillator of the pacemaker. The limiting circuit 17 is analogous to that of the embodiment of FIG. 1, and the circuit 18 has the function of polarizing the reference electrode and thus is provided only in case a system is fed from a single potential difference.

In practice, the particulars of execution may vary in an equivalent manner as to form, dimensions, arrangement and nature of the components within the scope of the present invention.

While specific embodiments of the invention have been shown and described in detail to illustrate the application of the principles of the invention, it will be understood that the invention may be embodied otherwise without departing from such principles.

What is claimed is:

1. In an artificial pacemaker including oscillator means providing electrical stimuli to the heart at the oscillator frequency, the improvement comprising, in combination, detector means operable to detect instantaneous variations of the pH of the blood as a function of the effort exerted by the wearer of the pacemaker to provide an electrical output which is a function of the instantaneous pH variation; and means connecting said detector means to said oscillator means to control the frequency of said oscillator means as a function of the detected pH of the blood.

2. In an artificial pacemaker, the improvement claimed in claim 1, in which said detector means effects a continuous electrometric measurement of the blood in vivo; said detector means including an indicating microelectrode of a precious metal of the platinum family, and a reference electrode coupled to said indicating microelectrode.

3. In an artificial pacemaker, the improvement claimed in claim 2, in which said indicating microelectrode is of the type Ir-IrO$_2$.

4. In an artificial pacemaker, the improvement claimed in claim 2, in which said reference electrode is of the type Ag-AgCl in a NaCl solution.

5. In an artificial pacemaker, the improvement claimed in claim 2, including an active impedance adapter connected in circuit with said indicating microelectrode and providing a high impedance of the order of several GOhms.

6. In an artificial pacemaker, the improvement claimed in claim 5, in which said connecting means comprises a d.c. amplifier connected to the output of said impedance adapter and amplifying, by at least 1000 times, the signal from said indicating microelectrode, having a potential difference of the order of a few mV, as adapted by said impedance adapter.

7. In an artificial pacemaker, the improvement claimed in claim 6, in which said oscillator is connected to the output of said d.c. amplifier and is a solid state oscillator of the astable type including transistors and in which variation of the frequency of the oscillator output is effected by polarization of the bases of the transistors by the output signal of said amplifier.

8. In an artificial pacemaker, the improvement claimed in claim 7, including a cathode follower connected to the output of said oscillator and furnishing the energy required for the impulses for the cardiac stimulation of the wearer of the artificial pacemaker.

9. In an artificial pacemaker, the improvement claimed in claim 8, including a limiting circuit connected to the input of said d.c. amplifier and fixing the minimum and maximum limit values of the stimulation frequency as well as fixing the scanning interval of the pH of the blood.

10. In an artificial pacemaker, the improvement claimed in claim 2, including an active impedance adapter connected in circuit with said indicating microelectrode and providing a high impedance of the order of $10^{12}$ ohms.

11. In an artificial pacemaker, the improvement claimed in claim 10, including a d.c. amplifier connected to the output of said impedance adapter and amplifying the output signal of said impedance adapter by at least 100 times.

12. In an artificial pacemaker, the improvement claimed in claim 11, including a unidirectional differentiator connected to the output of said d.c. amplifier and discriminating the output signal of said d.c. amplifier to exclude any signal due to drift to any origin and to render the pacemaker insensitive to alkaline variations of the blood.

13. In an artificial pacemaker, the improvement claimed in claim 12, including an a.c. amplifier connected to the output of said unidirectional differentiator and furnishing, as its output, a signal effective to control said oscillator.

14. In an artificial pacemaker, the improvement claimed in claim 13, in which said oscillator is a free oscillator controlled by the output signal of said a.c. amplifier and furnishing the energy required for the impulses for cardiac stimulation of the wearer of the artificial pacemaker.

15. In an artificial pacemaker, the improvement claimed in claim 14, including a limiting circuit connected to the output of said d.c. amplifier and to the input of said unidirectional differentiator, and affixing the minimum and maximum limit values of the stimulation frequency and the scanning interval of the pH of the blood.

16. In an artificial pacemaker, the improvement claimed in claim 15, including a polarization circuit connected to said reference electrode to polarize said reference electrode when the artificial pacemaker is supplied from a single potential difference.

* * * * *